United States Patent

Baffelli et al.

Patent Number: 5,597,553
Date of Patent: Jan. 28, 1997

[54] EXPANDED PERLITE TOOTHPASTE

[75] Inventors: Gianni Baffelli, Tesserete; Beat A. von Weissenfluh, Gentilino, both of Switzerland

[73] Assignee: Hawe Neos Dental Dr H.v. Weissenfluh AG, Bioggio, Switzerland

[21] Appl. No.: 302,758
[22] PCT Filed: Jan. 5, 1994
[86] PCT No.: PCT/CH94/00003
  § 371 Date: Sep. 13, 1994
  § 102(e) Date: Sep. 13, 1994
[87] PCT Pub. No.: WO94/15577
  PCT Pub. Date: Jul. 21, 1994

[30] Foreign Application Priority Data

Jan. 14, 1993 [CH] Switzerland ............ 00 104/93

[51] Int. Cl.$^6$ ............................................. A61K 7/16
[52] U.S. Cl. ............................................. 424/49
[58] Field of Search ............................... 424/49–58

[56] References Cited

U.S. PATENT DOCUMENTS

| 2,059,396 | 11/1936 | Ripert | 424/49 |
| 3,228,845 | 1/1966 | Najjar | 424/49 |
| 3,985,668 | 10/1976 | Hartman | 252/99 |
| 4,051,055 | 9/1977 | Trinh et al. | 252/95 |
| 4,051,056 | 9/1977 | Hartmann | 252/99 |
| 4,526,701 | 7/1985 | Rubin | 252/113 |
| 5,124,143 | 6/1992 | Muhlemann et al. | 424/49 |
| 5,266,304 | 11/1993 | Baffelli et al. | 424/49 |

FOREIGN PATENT DOCUMENTS

| 0268763A2 | 6/1988 | European Pat. Off. . |
| 0528756A1 | 2/1993 | European Pat. Off. . |

Primary Examiner—Shep K. Rose
Attorney, Agent, or Firm—Marks & Murase L.L.P.

[57] ABSTRACT

The toothpaste proposed contains as an abrasive, preferably as the sold abrasive, expanded perlite, generally with a particle size in the range of 1 to 150 μm, in particular with a main fraction in the region of 20 μm. This gives enhanced cleaning power, and improved protection of the tooth enamel against wear and scratching.

10 Claims, No Drawings

EXPANDED PERLITE TOOTHPASTE

This application claims the benefit under 35 U.S.C. §§ 120 and 371 of International Application No. PCT/CH 94/00003, filed Jan. 5, 1994 and published as WO94/15577 on Jul. 21, 1994.

The present invention refers to a toothpaste having improved cleaning properties and reduced hard dental substance abrasion effects (REA/RDA values).

Toothpastes are an everyday consumption product and are known as such in a great number of varieties. They generally contain a cleaning body which is dispersed in an aqueous phase, and various additives such as pigments, tensides, thickening agents, preserving agents, caries retarding fluorine compounds, flavouring agents and taste improving agents including sweetening agents and salts, as well as colouring agents. These additives shall establish a mouth hygiene and secure the acceptance of the toothpaste, especially by children.

The cleaning of the teeth is to be achieved by the cleaning body which should mechanically remove soiling matter during rubbing with the toothbrush, on one hand, but should not scratch the hard dental substance which is sensitive to scratching, on the other hand. Until now, it has been tried to solve this problem by incorporating hard minerals into the toothpaste, but they were used in a very finely divided form in order to avoid the formation of scratches in the hard dental substance.

The literature describes as cleaning bodies which have been used until now, for example and particularly the following finely divided substances, but the following listing is not to be intended as being complete and will only show that the problem of the correct choice of a cleaning body in toothpastes can by no means be regarded as solved: calcium carbonate, precipitated lime, whiting, pumice stone, calcium and magnesium phosphates, magnesium carbonate, barium carbonate, glass powder, zeolites, coral limestone, talcum, kaolin, bone substances, siliceous earth (kieselguhr), aluminium oxide, silicon dioxide, powdered synthetic materials, etc., in all possible variations. A review thereof is given in the Belgian BE-A-406,912 which further suggest to use, as a cleaning body, substances having a hardness which is not greater than that of the dental enamel, especially having a Mohs hardness between 2 and 3. Mica, asbestos and other substances are cited as examples which have no sharp edges in powder form but plane surfaces.

But this suggestion could not be satisfactory either since relatively soft cleaning bodies do not display the necessary cleaning effect during toothbrushing which should last at least about 5 minutes but which is not carried out for more than 1 to 2 minutes a day in an intensive manner.

It was an object of the present invention to develop a new toothpaste which now achieves a sufficient cleaning action in better protecting the hard dental substances even during relatively short treating times. The toothpaste of the invention is defined in the first independent claim whereas special embodiments thereof are the subject of dependent claims.

It has now surprisingly been found that a rock which is present in the form of sharp-edged particles which disintegrate when subjected to mechanical stress under the conditions of toothbrushing into still smaller, also sharp-edged particles, is very well suited as a cleaning body in the toothpaste. The originally present, relatively coarse particles having a size of the order of about 1 to 150 μm, the major portion being of about 20 μm, perform a very short-lasting but intensive cleaning action and are the immediately comminuted into still finer particles which then perform a desired, mild polishing action down to a finest polishing. In this way, a so-called "intelligently dynamical" cleaning and polishing action is obtained, and after the end of the toothbrushing, the surface of the teeth is smoothened such that the renewed deposit of residues on the teeth is impeded. A cleaning and polishing body having these properties and which is well suited is perlite, a rock which will be discussed further below.

Toothpastes for daily use which contain such cleaning bodies have not yet become known until now. The document EP-A2-0,268,763 discloses a dental care composition for the prophylactic dental hygiene and designs this composition sometimes as a toothpaste; however what is meant is a pasty dental hygiene composition applied by the dental hygienist once or twice a year by means of rotating brushes or little bowls. The composition described in that publication contains perlite and besides, as the most important component, specially prepared precipitated silicic acid. The action of the perlite is neither described nor indicated, it has not been recognised, and the one skilled in the art is guided to suppose that the perlite could be replaced by any other cleaning body whatsoever.

The patent application CH-A-2,437/91-8 of Aug. 19, 1991, of the same applicant and not published beforehand, relates to a dental care composition of the above described nature, i.e. an abrasive paste. In this patent application, the action of perlite in the field of dental care and in view of its physical and mechanical properties has been recognised; however, the described compositions must be free from water and must contain a stabiliser in the form of hydrophobic pyrogenic silicic acid. Furthermore, it is mentioned that perlite is unusable as a cleaning agent in dental care compositions which are present in aqueous phase since it is not active when not wetted and would require too great amounts of tensides on the ground of its high water absorbing capacity.

It has now surprisingly been found that perlite and similar substances can positively be used in an aqueous phase if a link is established between perlite particles and water. The effectiveness of perlite in aqueous phases and the stability of the toothpaste as a whole is achieved, according to the invention, by a synergistically active mixture of special tensides. This mixture comprises extremely pure sodium lauryl sulfate, sodium lauryl sarcosinate and a sodium taurid. The action of the perlite and the stability and the viscosity of the toothpaste are still better supported by a pyrogenic silicic acid which has also a cleaning action and which has been made hydrophilic, and acts as a binder, a structuring agent and a thixotropic agent.

Perlite is a rhyolithic-vitreous rock of volcanic origin and is basically a sodium potassium aluminium silicate containing about 73% of $SiO_2$, 13% of $Al_2O_3$, 1% of $Fe_2O_3$, below 0.5% of $MgO$, 3.3% of $Na_2O$, 4% of $K_2O$ and 2 to 4% of water. The percentages refer here and in the whole document to the weight if not otherwise indicated. Particles of this rock obtained by grinding have the property of exploding on heating due to their water content. This seems to be a special property which is occurring with perlite only. In the frame of the present invention, only the exploded (expanded) perlite is considered and used.

Perlite owns, like the other rocks of its group, e.g. ignimbrite, tuff, trass, etc., an inner cell structure, and the fragments obtained by grinding and remaining after classifying rememeber broken eggshells under the microscope, i.e. sharp edged and often arched shell-like objects. When these shells are further comminuted, a scaled down image is originated until reaching a very fine powder.

It is preferred to use in the toothpaste of this invention a perlite fraction obtained by classifying which comprises particles having a size between about 1 and 150 μm, about 90% thereof being in the range of from 5 to 90 μm, the most frequent size being about 20 to 25 μm. The selection of such a fraction was surprising since the toothpastes known until now which contain abrasive bodies having a similar chemical composition, for example pumice, comprise such bodies having a particle size of from about 1 to 10 μm and a most frequent occurrence of about 3 to 4 μm.

The pyrogenic silicic acid acting as a stabiliser and a thixotropic agent is also known under the name of fumed silica ("aerosil") and can be obtained, e.g., by the thermal decomposition of silicon tetrachloride in an oxyhydrogen flame and in the presence of water. Amorphous, spherical particles are obtained having a diameter of 20 to 40 nm and a specific surface area of 100 to 400 m$^2$/g. By reaction of superficial SiOH groups with suitable reagents, the pyrogenic silicic acid can be made hydrophilic according to known methods. The toothpaste of the invention contains this hydrophilic pyrogenic silicic acid which is commercially available, generally in a weight ratio of from 12:1 to 1:3, indicated as the ratio of perlite to pyrogenic silicic acid.

The toothpaste of the invention contains, as it has already been shortly mentioned above, further additives which should bring about the adaptation to the usability and the acceptance and which further achieve additional effects. Thus, the toothpaste may contain, as it is customary today, fluorine compounds for caries prophylactics; suitable fluorine compounds are known to the one skilled in the art. Further generally usual additives are wetting agents such as glycerol, sorbitol and other sugars, e.g. disaccharides and/or sugar alcohols as well as polyethylene glycols which may also act as sweetening agents or structuring agents; real, natural or synthetic sweetening agents such as saccharin or sweetening peptides etc.; binding and thickening agents, e.g. cellulose esters and ethers such as carboxymethyl celluloses; preserving agents such as hydroxybenzoates; colouring agents, flavouring agents such as peppermint oil, pigments and, in special cases, additional other abrasive bodies such as calcium carbonate. All these additives are generally usual and are known to the one skilled in the art.

A preferred toothpaste of the invention has the following composition by weight:

aqueous liquid of water and glycerol, sorbitol, disaccharide syrup, etc. 55 to 85% sweetening agent 0.1 to 0.5% organic thickening agent 0 to 3% polyethylene glycol 0 to 6% preservative, fluorine compounds, colouring and flavouring agents, pigments 0.5 to 12% tenside mixture as defined above 2 to 5% perlite, av. particle size about 20 to 25 μm 1 to 12% pyrogenic silicic acid 1 to 3%

Regarding the long-time use of a toothpaste, its abrasive properties are of particular importance since it must not happen that the hard tooth substance is damaged by a regular use of the toothpaste. Therefore, sensitive measuring techniques have been introduced and standard values of abrasion have been developed which define a maximum permissible abrasion of the substrate or the hard dental substance, respectively, on which the toothpaste is acting.

A rough orientation of the abrasion effects is obtained by the treatment of copper plates by a toothpaste under definite conditions and subsequent determination of the copper loss. However, this method is too inexact.

Nowadays, the so-called RDA/REA method has been introduced. It is based on a measurement of radioactivity. Extracted human or animal teeth which have been made radioactive in a definite manner, are treated with the toothpaste to be tested, and the radioactivity of the toothpaste transferred into a suspension after treatment is measured. The higher are these values, the greater was the abrasion. The RDA value refers to the dentine and the REA value to the hard dental substance, the enamel. This method has been reported in the Journal of Dental Research 55 (4), 563 (1976).

The toothpaste of the invention was now examined, and a known, commercially widespread toothpaste served as a comparison. The comparative paste, called Paste V in the following, contained a cleaning body having a particle size of 3 to 4 μm (main portion). The RDA value measured with Paste V was 82, and the RDA value of the toothpaste of the invention which contained 6% of perlite, 67. However, the toothpaste of the invention had a cleaning power of 155, measured according to a conventional method during 30 seconds whereas Paste 5 had a power of 100. Since the hard dental substance abrasion must be referred to the same cleaning power, the toothpaste of the invention thus has a relative RDA value of about 43, and Paste V such a value of 82. The abrasion, caused by the toothpaste of the invention, is therefore only about the half of that of the comparative paste.

Another toothpaste of the invention which contained only 3% of perlite and was otherwise identically composed as the toothpaste tested above, had a RDA value of about 20 while the cleaning power decreased by about 25% only. This toothpaste thus achieves still much more favourable abrasion conditions.

The toothpaste of the invention may further be modified and perfected within the frame of the following claims. Thus, it is for example possible to incorporate a further abrasive body; such secondary abrasive bodies which are already known per se, may be taken from the present description.

We claim:

1. A toothpaste having improved cleaning power, containing an aqueous liquid and an abrasive body, characterized in that the toothpaste contains as the sole abrasive body expanded perlite which is present in the form of sharp-edged particles which disintegrate by mechanical stress under the conditions of toothbrushing into smaller, also sharp-edged particles, and wherein said abrasive body is present in the toothpaste in an amount of from 1% to not more than 15% by weight.

2. The toothpaste of claim 1, characterised in that it contains the said perlite fraction as the sole abrasive body.

3. The toothpaste of claim 1 characterised in that the toothpaste further contains a finely divided pyrogenic silicic acid which has been made hydrophilic, as a binder and a viscosity regulator.

4. The toothpaste of claim 2, characterised in that it contains as a perlite fraction such a fraction which has a most frequent average particle size of from 20 to 25 μm, particles having sizes below 1 μm and exceeding 150 μm being absent, and that the fraction between 20 and 25 μm amounts to about 50% by weight of the total fraction.

5. The toothpaste of claim 1, characterised in that it contains from 1 to 12% by weight of perlite.

6. The toothpaste of claim 5, characterised in that it contains from 1 to 6% by weight of perlite.

7. The toothpaste of claim 5, characterised in that it contains from 1 to 3% by weight of perlite.

8. The toothpaste of claim 3, characterised in that the weight ratio of perlite to pyrogenic silicic acid is comprised between 12:1 and 1:3.

9. The toothpaste of claim 1, characterised in that it contains a tenside mixture composed of extremely pure sodium lauryl sulfate, sodium lauryl sarcosinate and a sodium taurid.

10. The toothpaste of claim 9, characterised in that it has the following composition, given by weight:

aqueous liquid of water and glycerol, sorbitol, etc. 55 to 85% artificial sweetening agent 0.1 to 0.5% organic thickening agent 0 to 3% polyethylene glycol 0 to 6% preservative, fluorine compounds, colouring and flavouring agents, pigments 0.5 to 12% tenside mixture 2 to 5% perlite, av. particle size about 20 to 25 μm 1 to 12% pyrogenic silicic acid 1 to 3%.

* * * * *